(12) United States Patent
Narahara et al.

(10) Patent No.: US 11,618,028 B2
(45) Date of Patent: Apr. 4, 2023

(54) DEVICE FOR NUCLEIC ACID AMPLIFICATION REACTION

(71) Applicant: MIZUHO MEDY CO., LTD., Saga (JP)

(72) Inventors: Kenji Narahara, Saga (JP); Takashi Nagano, Saga (JP); Shinya Motomatsu, Saga (JP)

(73) Assignee: MIZUHO MEDY CO., LTD., Saga (JP)

( * ) Notice: Subject to any disclaimer, the term of this patent is extended or adjusted under 35 U.S.C. 154(b) by 612 days.

(21) Appl. No.: 16/463,517

(22) PCT Filed: Nov. 9, 2017

(86) PCT No.: PCT/JP2017/040453
§ 371 (c)(1),
(2) Date: May 23, 2019

(87) PCT Pub. No.: WO2018/105302
PCT Pub. Date: Jun. 14, 2018

(65) Prior Publication Data
US 2019/0374951 A1    Dec. 12, 2019

(30) Foreign Application Priority Data

Dec. 8, 2016 (JP) ............................ JP2016-238677

(51) Int. Cl.
*C12Q 1/68* (2018.01)
*B01L 7/00* (2006.01)
*C12Q 1/6844* (2018.01)

(52) U.S. Cl.
CPC .............. *B01L 7/52* (2013.01); *C12Q 1/6844* (2013.01)

(58) Field of Classification Search
CPC ......... B01L 2200/028; B01L 2200/027; B01L 2200/026; B01L 2300/0681; B01L 2300/0825; B01L 2300/069; B01L 3/5023
(Continued)

(56) References Cited

U.S. PATENT DOCUMENTS

2006/0194207 A1   8/2006 Mitani et al.
2009/0186357 A1 * 7/2009 Mauk .................... B01L 3/5027
                                                435/6.15
(Continued)

FOREIGN PATENT DOCUMENTS

JP       2003-512032      4/2003
JP       2004-350649     12/2004
(Continued)

OTHER PUBLICATIONS

Bej et al. (Appl and Envrion Microbiol, 1992, 57(12):3529-3534) (Year: 1992).*
(Continued)

*Primary Examiner* — Stephanie K Mummert
(74) *Attorney, Agent, or Firm* — Wenderoth, Lind & Ponack, L.L.P.

(57) ABSTRACT

This device comprises: a casing with an upper surface including a sample-dripping portion receiving a liquid sample containing nucleic acid and being dripped from a nozzle; a reaction tube: outwardly projecting from an end of the casing; including a storage space therein; and being formed so as to be installed within a measurement apparatus; a filter carrying the nucleic acid contained in the liquid sample; a filter-supporting body stored within the casing to support the filter in a manner such that the filter is capable of taking: a contacting position wherein the filter contacts with the liquid sample right below the sample-dripping portion; and a reaction position wherein the filter is posi- (Continued)

Figure 1:
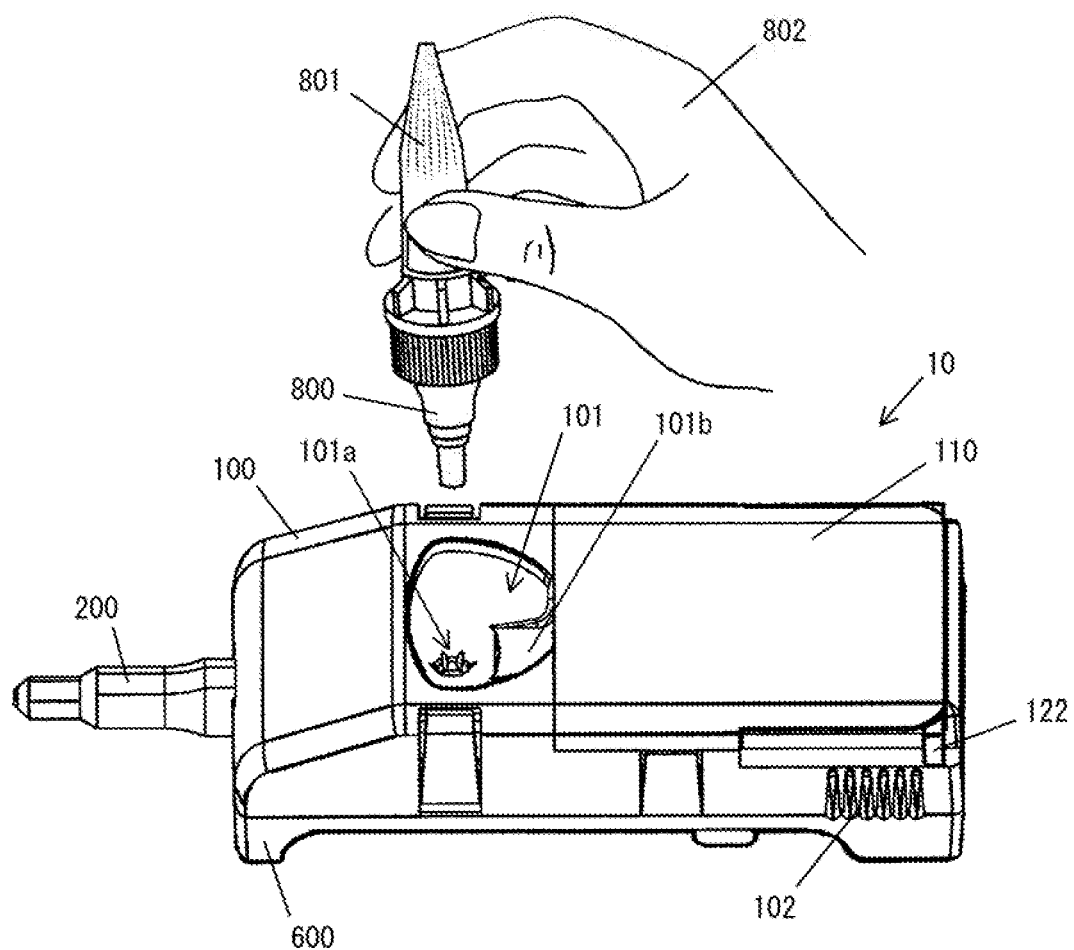

tioned within the storage space of the reaction tube; and absorbing material capable of taking: a press-attaching position wherein the absorbing material is press-attached to the filter in the contacting position so that the filter absorbs the liquid sample contacting therewith; and a separating position wherein the absorbing material is removed from the press-attaching position so that the filter is allowed to freely move.

11 Claims, 12 Drawing Sheets

(58) Field of Classification Search
USPC .......................................................... 137/829
See application file for complete search history.

(56) References Cited

U.S. PATENT DOCUMENTS

| | | | |
|---|---|---|---|
| 2011/0059433 A1 | 3/2011 | Marc et al. | |
| 2011/0212453 A1* | 9/2011 | Agarwal | B01L 3/52 435/6.12 |
| 2011/0244466 A1* | 10/2011 | Juncosa | B01L 3/502 435/6.12 |
| 2014/0273198 A1 | 9/2014 | Saito et al. | |
| 2016/0310948 A1 | 10/2016 | Nowakowski et al. | |
| 2016/0340714 A1 | 11/2016 | Siciliano et al. | |
| 2017/0028362 A1* | 2/2017 | Stasiak | B01D 67/0083 |

FOREIGN PATENT DOCUMENTS

| | | | |
|---|---|---|---|
| JP | 2006-518221 | 8/2006 | |
| JP | 2008-538910 | 11/2008 | |
| JP | 2014-89201 | 5/2014 | |
| JP | 2014-176306 | 9/2014 | |
| WO | 01/28683 | 4/2001 | |
| WO | 02/18902 | 3/2002 | |
| WO | WO-03093796 A2 * | 11/2003 | .......... B01L 3/50255 |
| WO | 2004/003541 | 1/2004 | |
| WO | 2005/012518 | 2/2005 | |
| WO | 2006/071770 | 7/2006 | |

OTHER PUBLICATIONS

International Search Report dated Feb. 13, 2018 in International Application No. PCT/JP2017/040453.

* cited by examiner

DEVICE FOR NUCLEIC ACID AMPLIFICATION REACTION

BACKGROUND OF THE INVENTION

1. Field of the Invention

The present invention relates to a device used for nucleic acid amplification so as to detect and/or identify base sequence of target nucleic acid.

Upon using the device used for nucleic acid amplification with a simple measurement apparatus, the present invention becomes preferably applicable in a clinical site in a mode of POCT.

The word of "POCT" is an abbreviation for "Point of Care Testing", which means a test conducted near a subject and/or conducted by the subject himself/herself. POCT possesses benefit of: shortening of test time; and carrying out in the clinical site, which is a test that can be seen by the subject himself/herself.

POCT is also defined as a test for improving quality of quick and suitable medical care, nursing, preventing illness, health care, QOL (Quality of life), and the degree of satisfaction thereof in the POCT guideline issued by the Japan society for clinical laboratory automation.

2. Description of the Related Art

In recent years, the field of life science has been remarkably developed, and technique for analyzing nucleic acid (such as DNA, RNA, or the like) has been widely used.

The nucleic acid-analyzing technique is used for:
identification of species and/or study of origin in the biological field;
diagnosis of diseases in the medical field;
specifying the place of agricultural product; and/or
judging the existence of gene recombination for safe and security of food in the field near everyday life, for example.

With respect to diagnosis of diseases in the medical field, in particular with respect to rapid diagnostic of infectious diseases, technique (hereinafter, called as "genetic screening") of amplifying and/or analyzing (by means of a PCR method, a method for isothermal nucleic acid amplification, or the like) target nucleic acid, such as characteristic gene sequence of a foreign gene that does not exist in oneself among nucleic acid-analyzing technique is excellent in sensitivity and specificity thereof as compared with conventional infectious disease diagnostic technique such as a culture test, immunological examination (a test using antigens and/or antibodies).

In accordance with the genetic screening, it is possible to detect and/or identify almost all kinds of pathogenic microorganisms that cause Homo sapiens infectious diseases, such as bacteria, funguses, protozoon, viruses, or the like.

For this reason, the genetic screening is frequently used in large-scaled facilities with rich staffs, for example, large-scaled hospitals with dedicated inspecting rooms and/or laboratories, institutes of health, and research facilities of universities and companies.

The market of the genetic-screening utilizing diagnostic reagent has expanded every year. It is thought that the genetic-screening will increase importance thereof with respect to not only a point of view of rapid diagnosis of infectious-diseases but also another point of view of economic activities.

However in practice, the genetic screening is rarely used in medical facilities where ordinary persons tend to visit many times, for example, familiar private hospitals, clinics, or the like.

As a reason of the above, it may be adduced that the genetic screening beforehand requires reagent preparation and pretreatment of nucleic acid, which are so complicated and take a long time.

For this reason, it is difficult to correspond to the preparation and the pretreatment simultaneously with business other than the same. In the above small facilities, the burden of the same is too heavy, and the labor of the members cannot be limited to the genetic screening. Such a problem may be adduced.

As another reason, initial investment costs and administrative and maintenance expenses are too high for such the above small facilities. In order to perform the above pretreatment of nucleic acid, physical and chemical equipment such a centrifugal machine and a micropipette must be provided, and automating equipment for the genetic screening must be also introduced. Such a problem may be adduced.

As a further other reason, almost all of the members such as doctors and/or nurses within such the above small facilities are not skilled in the genetic screening enough. Such a problem may be adduced.

To the contrary, also in the above small medical facilities without an dedicated inspecting room and/or laboratory, test kits corresponding to the POCT based on immunological examination (for example, a labeled antibody method, an immunonephelometry method, a latex flocculation method, an immunochromatography method) are widely used for diagnosis of infectious diseases.

For example, the Japan Ministry of Health, Labor and Welfare has announced that an amount of rapid examination kits regarding influenza antigens scheduled to be provided (2015/2016) are for about 27,950,000 persons. Due to this, it is thought that POCT rapid examination kits regarding influenza antigens have already spread all over Japan.

However, with respect to rapid diagnosis of infectious diseases in an early stage, in particular with respect to rapid diagnostic of infectious diseases, in some cases, separating and cultivating pathogenic microorganisms from a specimen may be performed. This is because the concentration of antigens and/or antibodies contained within the specimen is too low for the immunological examination to obtain a sufficient inspection result.

The separating and the cultivating pathogenic microorganisms require aseptic processing by an operator with dedicated equipment and special information and several days, which needs hard labor and a long time. Except the large-scaled hospitals, university hospitals, or the like, it is impossible to easily perform such operation.

Furthermore, there are some kinds of microorganisms that are difficult to cultivate.

On the other hand, the genetic screening of target nucleic acid is considered to possess sensitivity higher than that of the immunological examination. The genetic screening is very effective in a case where it is difficult to secure antigens and/or antibodies, and another case where a detection result with high sensitivity is needed.

There is not, however, such a kit for the genetic screening facilitated just like the POCT kit according to the immunological examination.

Accordingly in many cases, the genetic screening is rarely carried out in the small medical facilities, or the like. Thus, in the small medical facilities, the specimens are only collected to be sent to an external facility for test consignment. This results in taking a long time until knowing the result thereof.

Therefore, it is very helpful to transform the genetic screening in a manner of POCT. This is because it makes possible for also the small medical facilities to perform rapid genetic screening by themselves, thereby resolving the above-mentioned problems regarding the rapid diagnosis of infectious diseases.

Herein, process of the genetic screening currently carried out can be roughly divided into the following four steps. That is:

(1) a first step of:
collecting a specimen; and
then destroying cell walls and/or cell membrane thereof to expose intracellular nucleic acid to be caught by a solid-phase carrier or the like;

(2) a second step of:
washing, removing, and separating contaminant therein, such as protein, by means of organic solvent, or the like; and
isolating only the nucleic acid;

(3) a third step of:
amplifying the target nucleic acid according to nucleic acid amplification reaction by means of a mold of the separated nucleic acid; and (4) a fourth step of:
after the nucleic acid amplification reaction, detecting the amplified target nucleic acid directly or indirectly by means of probes with markers; and
performing qualitative analysis and/or quantitative analysis thereof Upon conducting the genetic screening in general, the four steps are performed one by one according to manual operation thereof and/or utilizing individual physical and chemical equipment suitable for each of the four steps. In this way, the work must be so complicated and must take a long time.

More concretely, during the pretreatment process operation, solvent preparation, centrifugal separation, and drying may be performed, and during the nucleic acid amplification reaction, a lot of kinds of reagent components should be isolated and mixed to prepare the reagent for the nucleic acid amplification reaction.

In practice during the nucleic acid amplification reaction, the temperature should be repeatedly increased and decreased. Thus, a dedicated device (ex. a thermal cycler) for changing the temperature is also required.

The amplified products may be detected according to various ways, for example, gel electrophoresis and/or a method of measuring signals of fluorescent substance of the probes. Anyway, dedicated measurement apparatuses must be prepared to need a long time and huge costs in view of this point.

An amount of several [μL] of enzyme or the like through dozens of [μL] of the enzyme or the like is dispensed during the reagent preparation. However, the amount is so minute that the dispensing may be forgotten and/or be carried out erroneously. There is also a problem that contamination may easily occur during such a lot of operation steps.

In view of such conditions, an one packaged device wherein all of the steps of: catching nucleic acid; washing thereof; performing nucleic acid amplification reaction thereon; and detecting thereof has also been devised.

Document 1 (Japanese Translation No. 2006-518221 of PCT application) discloses a method of processing a sample.

In Document 1, a reagent device including: nine segments divided with peel-able seals; and beforehand packed reagent to be used is disclosed.

The respective necessary reagent liquid is filled and sealed within the respective segment among the nine segments of a flexible small tube.

By controlling the device according to complicated operation, an actuator and a cramp are applied onto the respective segment so as to sequentially release and push out the segments, respectively. In this way, the above steps of: mixing the respective reagent liquid; and washing thereof and so on are carried out.

Finally, genes caught by magnetic silica beads and washed are eluted within reaction solution, and pass through the amplification reaction to be detected.

When a magnetic field resource generates a magnetic field, the magnetic silica beads catch the genes. On the other hand, when the magnetic field resource removes the magnetic field, the magnetic silica beads releases the genes.

Thus, all of necessary steps can be completed within one device. It is hard to prepare and seal the respective reagent to the respective area in the device.

The device, however, requires both of the complicated control mechanism and the magnetic field resource. It must be said that the degree of technical difficulty is very high and that costs for manufacturing the device and apparatuses become also expensive considerably.

Document 2 (Japanese Patent Application Laid-open No. 2014-89201) discloses a fluid control processing system.

According to Document 2, the fluid control processing system is provided (within a device) with a plurality of chambers including: a sample chamber; a solution chamber; a washing chamber; a disposal chamber; and a main mixture chamber.

The fluid control processing system is further provided with at least one port selectively connecting the chambers according to the rotation of rotary valves. Thus, necessary liquid components pass through micro flow paths, and steps of pretreatment of genes are sequentially performed.

The liquid components are transported according to force of depression and/or compression caused by up-and-down motion of a piston. The mixture within the main mixture chamber passes through branches to move toward a reaction vessel, and then amplification reaction and detection regarding the same are carried out.

Thus, according to Document 2, all of necessary steps can also be completed within one device. It is also, however, hard to prepare and seal the respective reagent to the respective area in the device.

The device requires both of the complicated control mechanism including the piston and the rotation of the rotary valves within the measuring apparatus. It also must be said that costs for manufacturing the device and the apparatuses become expensive considerably.

LIST OF RELATED DOCUMENTS

Document 1: Japanese Translation No. 2006-518221 of PCT application

Document 2: Japanese Patent Application Laid-open No. 2014-89201

OBJECTS AND SUMMARY OF THE INVENTION

In view of the above, an object of the present invention is to provide a device for nucleic acid amplification reaction capable of performing the genetic screening and the nucleic acid amplification reaction at ease, safely, and rapidly.

A first aspect of the present invention provides a device for nucleic acid amplification reaction, comprising: a casing with an upper surface including a sample-dripping portion receiving a liquid sample containing nucleic acid and the liquid sample being dripped from a nozzle; a reaction tube: outwardly projecting from an end of the casing; including a storage space therein; and being formed so as to be installed within a measurement apparatus; a filter carrying thereon the nucleic acid contained in the liquid sample; a filter-supporting body stored within the casing to support the filter in a manner such that the filter is capable of taking: a contacting position wherein the filter contacts with the liquid sample right below the sample-dripping portion; and a reaction position wherein the filter is positioned within the storage space of the reaction tube; and absorbing material capable of taking: a press-attaching position wherein the absorbing material is press-attached to the filter in the contacting position so that the filter absorbs the liquid sample contacting therewith; and a separating position wherein the absorbing material is removed from the press-attaching position so that the filter is allowed to freely move.

A second aspect of the present invention provides, in addition to the first aspect, further comprising: a cleaning liquid pot carrying cleaning fluid therein; and a member allowing the cleaning fluid within the cleaning liquid pot to flow toward the sample-dripping portion.

It is preferable that a pressing part drives the filter-supporting body to be supported so that the filter-supporting body is allowed to move from the contacting position to the reaction position.

It is preferable that the reaction tube is composed of a transparent material.

It is preferable that at least the part of reagent required for the nucleic acid amplification reaction contains hot-melt polymeric compound that is solidified and/or gelled before the nucleic acid amplification reaction, and that is heated to become liquid in the nucleic acid amplification reaction, at least the part of reagent being held within the reaction tube.

It is preferable that the absorbing material is composed of a water absorptive soft material including filter paper, a polymeric absorbing material, and glass fiber filter paper.

It is preferable that a silica particle is fixed to the filter.

It is preferable that the filter is composed of polymeric membrane.

It is more preferable that the filter is composed of hydrophilic PTFE (polytetrafluoroethylene).

It is preferable that the filter-supporting body holds at least the part of the reagent required for the nucleic acid amplification reaction.

EFFECT OF INVENTION

According to the present invention, the following benefit is obtained.

(1) Since it is unnecessary for an operator to carry out complicated reagent preparation and operation steps, genetic screening can be performed rapidly and easily.

(2) Precise genetic screening with high sensitivity can be carried out. Furthermore, the problem of contamination in the genetic screening that tends to occur in general can be solved.

(3) In addition, the above arrangement of the device for nucleic acid amplification reaction enables to perform the steps of: catching genes; washing the same; amplification of the same, and so on in accordance with only simple driving operation. Costs for both of the measurement apparatus and the genetic screening are also reduced.

DETAILED DESCRIPTION OF THE PREFERRED EMBODIMENTS (Gist of Invention)

Prior to concrete explanation of Embodiments, the gist of the present invention will now be described.

The device for nucleic acid amplification reaction is configured so as to function according to comparatively easy operation. In other words, operation mechanism for the same can be also simplified. As a result, a dedicated measurement apparatus for the same can be also manufactured reasonably.

In this way, upon utilizing the genetic screening system according to the present invention, the screening can be done at ease, rapidly, and at a low cost.

According to the present invention, almost all of the necessary components exist within a device for nucleic acid amplification reaction 10, and it is sufficient to prepare only a few kinds of reagent. And, operation is easily carried out by simply driving the dedicated measurement apparatus.

Firstly, there is a merit of the production costs for both of the reagent and the measurement apparatus. Secondly, it is thought that troubles during measurement operation can also be reduced.

According to the present invention, it is enough for an operator to drip a liquid sample onto a sample-dripping portion 101 of the device 10 and to set the dripped device 10 to the dedicated measurement apparatus 700. If so, the operator will be able to obtain a result thereof after predetermined reaction time.

When the device 10 is inserted into the measurement apparatus 700, the reaction tube 200 of the device 10 is inserted into and firmly fixed to the temperature control block 703 of the measurement apparatus 700. In the temperature control block 703, nucleic acid amplification reaction is carried out.

An important point of the present invention is as follows. Firstly, genes within the liquid sample dripped onto the sample-dripping portion 101 are caught and washed on the filter 301 within the device 10. And, after that secondly, the genes are moved into the reaction tube 200 wherein the nucleic acid amplification reaction is carried out.

In an initial state before measurement, the filter 301 and the reaction tube 200 within the device 10 are separately positioned, respectively. A liquid sample is dripped onto the sample-dripping portion 101. Then, target genes are caught on the filter 301, when the liquid sample passes through the filter 301.

The first pressing element 1 provided with the measurement apparatus 700 is driven to move the cleaning liquid pot 120 sealing cleaning fluid therein, the cleaning fluid within the same pot 120 is supplied to the filter 301 to wash the genes.

The filter 301 is carried by the filter-supporting body 300. In the inside of the device 10, the support 501 abuts onto both of the absorbing material installation plate 400 and the filter-supporting body 300 so as to press-attach the absorbing material 401 onto the filter 301.

When the second pressing element 2 of the measurement apparatus 700 is driven to make the support 501 move, the filter-supporting body 300 and the filter 301 are released from the press-attached state so as to become capable of moving.

The third pressing element 3 of the measurement apparatus 700 moves the filter-supporting body 300 (in particular, a driving rib 303) so as to make the filter 301 move toward a deep portion of the inside of the reaction tube 200. As a result, the filter 301 contacts with the reagent 201.

In this way, the washed genes in the liquid sample caught by the filter 301 are also inserted into the reaction tube 200.

Nucleic acid amplification reaction can be performed using the inserted genes and the reagent 201 for nucleic acid amplification reaction that has been in advance filled up while the temperature control block 703 of the measurement apparatus 700 controls the temperature thereof by heating and/or cooling the same repeatedly.

More concretely as shown in FIG. 1, firstly, an operator collects a patient specimen in the dedicated extraction container 801 in order to extract genes contained therein. And secondly, the operator drips a liquid sample onto the sample-dripping portion 101 of the device 10 by means of the dripping nozzle 800.

Figure 2:
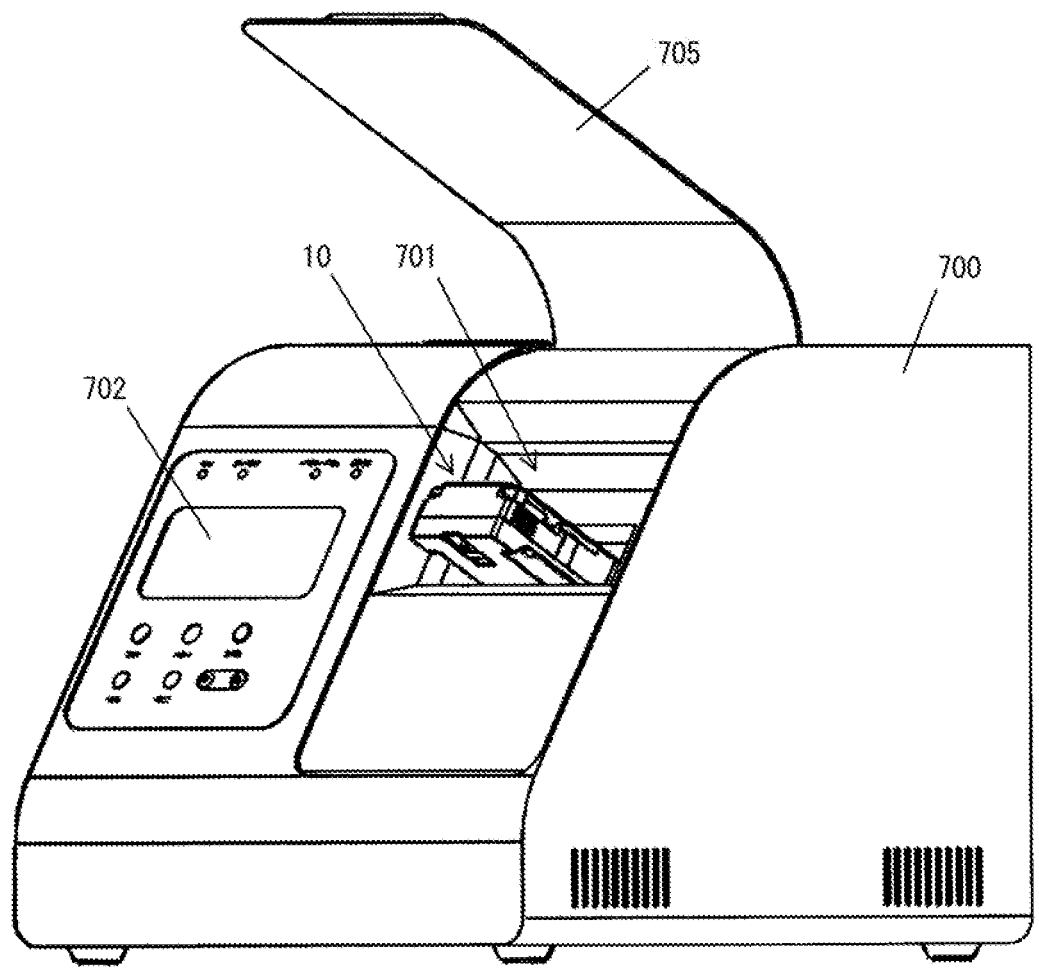

As shown in FIG. 2, after having confirmed that the liquid sample has been absorbed, the operator inserts this device 10 into the dedicated measurement apparatus 700.

The genes within the dripped sample are caught on the filter 301 carried by the filter-supporting body 300, and unnecessary liquid is removed by being absorbed by the absorbing material 401 press-attached to a lower surface of the filter 301.

In order to improve catching efficiency of the genes, it is preferable to apply silica particles onto the filter 301.

The cleaning liquid pot 120 in which cleaning fluid has been filled up is set to the inside of the device 10 movably, and an injecting port of the cleaning liquid pot 120 is sealed by means of a breakable member.

When the first pressing element 1 of the measurement apparatus 700 applies force to the cleaning liquid pot 120 from the outside thereof, the cleaning liquid pot 120 moves. When the breaking projection 111 within the device 10 breaks through the breakable sealing member, the internal cleaning fluid is discharged to the sample-dripping portion 101 via the chute 101b.

After having washed the genes on the filter 301, the cleaning fluid passes through the filter 301 to be absorbed by the absorbing material 401.

Herein, it is necessary that the liquid sample and the cleaning fluid supplied from the sample-dripping portion 101 smoothly pass through the filter 301 according to a capillary phenomenon to leach out toward the absorbing material 401 at the lower surface.

Accordingly, the sample-dripping portion 101 and the absorbing material 401 are press-attached to each other so that they are firmly fitted in a vertical direction.

The absorbing material 401 has a volume that can fully absorb liquid therein, and is fixed to the absorbing material installation plate 400. Furthermore, the absorbing material installation plate 400 is supported by the support plate 500 from a lower side so that the filter 301 is indirectly press-attached to the absorbing material 401.

When the second pressing element 2 of the measurement apparatus 700 makes the support plate 500 move, the placing part 402 of the absorbing material installation plate 400 is separated from the support 501, and the absorbing material installation plate 400 is released together with the filter-supporting body 300 from the press-attaching state.

In this way, the filter 301 of the filter-supporting body 300 is also released from the press-attaching state wherein the filter 301 is fitted between the sample-dripping portion 101 and the absorbing material 401.

After that, the third pressing element 3 of the measurement apparatus 700 makes the filter-supporting body 300, in particular the driving rib 303, move so that the filter 301 is inserted into the reaction tube 200.

The reaction tube 200 has in advance contained therein the reagent 201 required for both nucleic acid amplification reaction and detection of the genes, and the reagent 201 is fixed when the filter 301 has been inserted in the temperature control block 703 of the measurement apparatus 700.

The genes caught by the filter 301 of the filter-supporting body 300 moves into the reaction tube 200 to contact with the reagent 201. After that, the amplification reaction regarding the genes can be performed by controlling temperature (increasing/decreasing the temperature thereof repeatedly, or the like.) by means of the temperature control block 703 of the measurement apparatus 700.

After the amplification reaction has been completed, the fluorescence measurement unit 704 of the measurement apparatus 700 can detect amplified product within the reaction tube 200 so as to judge the existence of the target genes.

According to the present invention, the internal arrangement and the system of the device 10 are configured as mentioned above. Therefore, it is sufficient for the operator to drip the liquid sample thereto and to set thereof into the dedicated measurement apparatus 700 only. This simple operation enables to carry out the genetic screening rapidly and easily.

Embodiments of the present invention will now be described more concretely with reference to the accompanying drawings.

Figure 3:
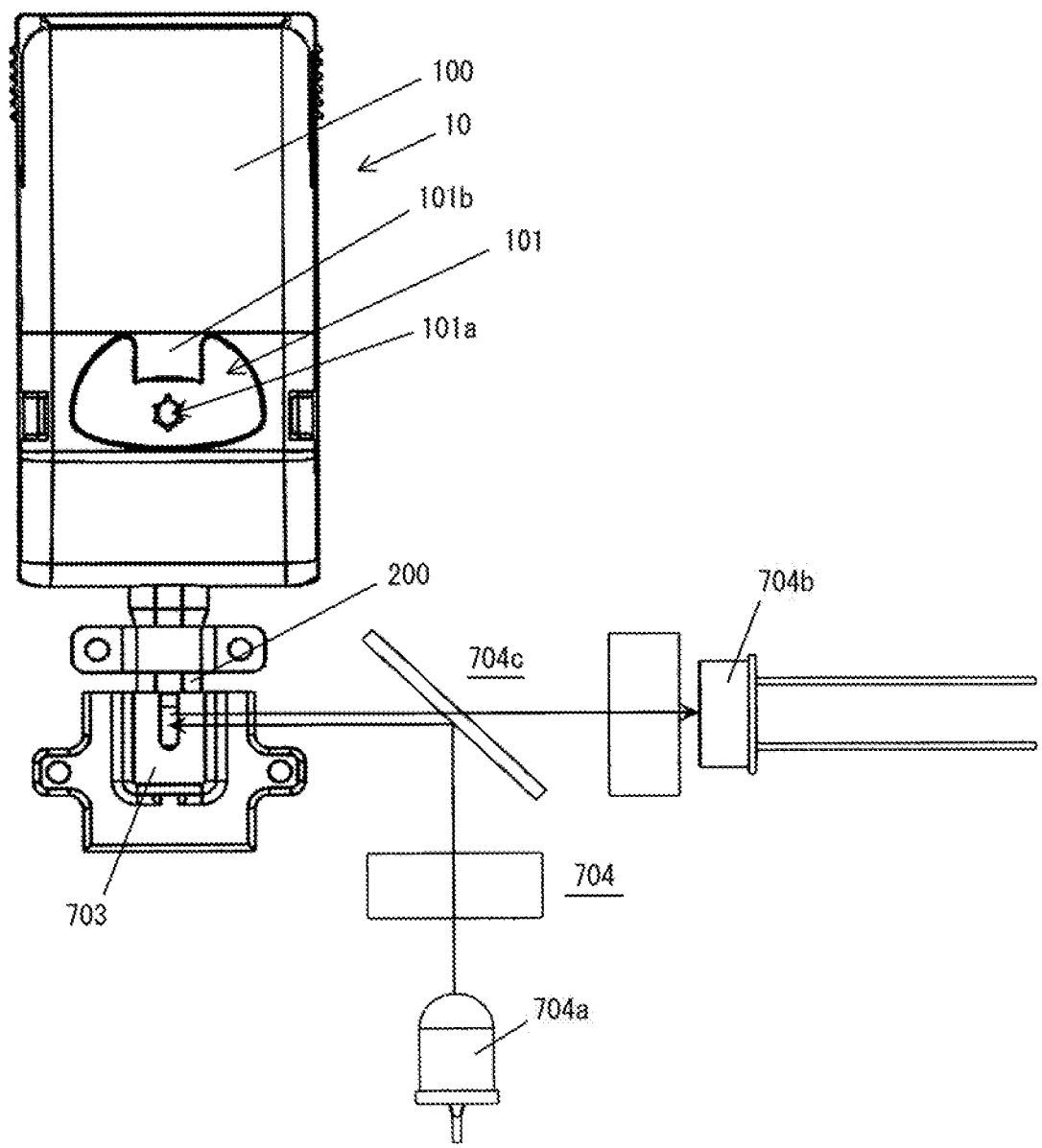
Figure 4:
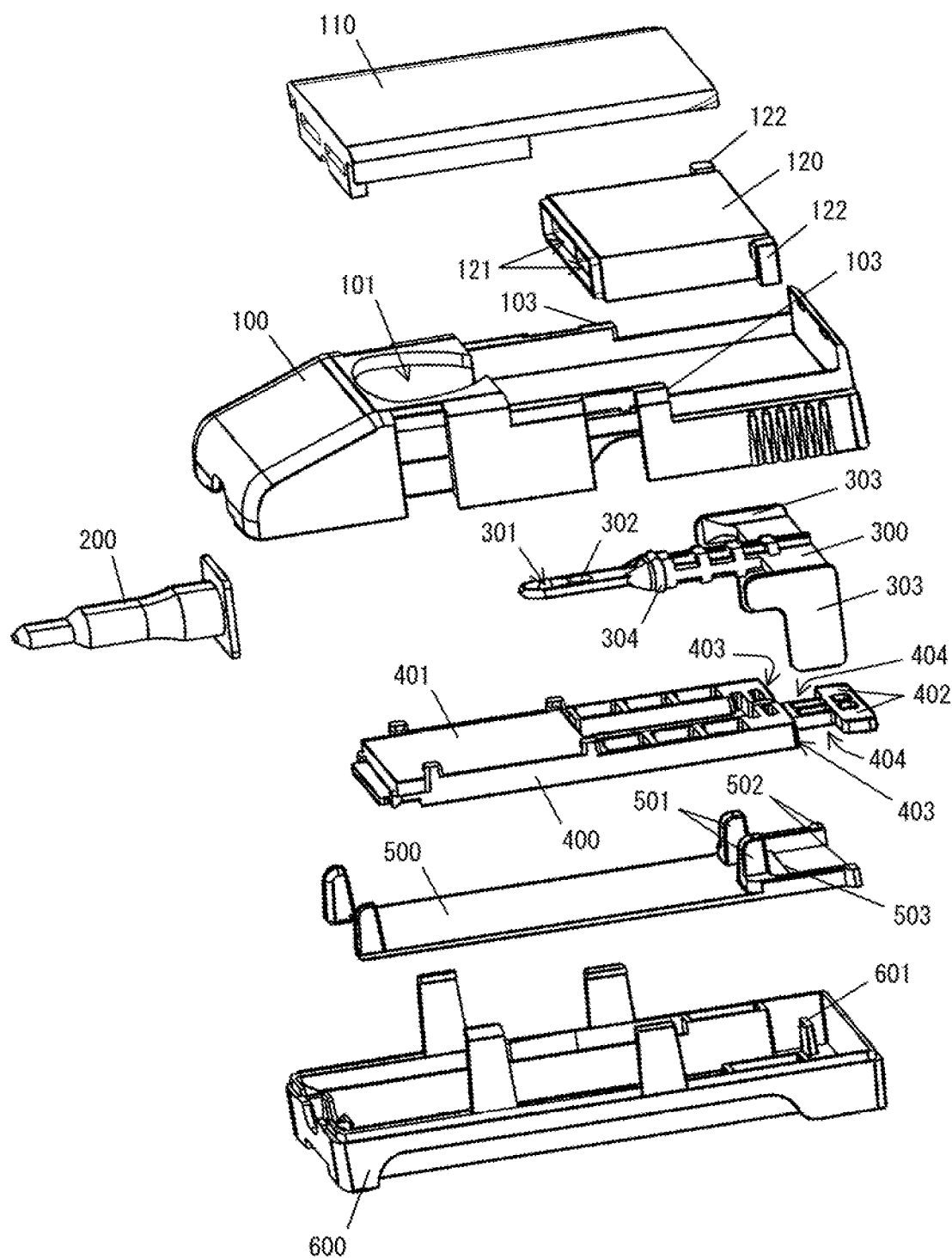

FIG. 1 is a perspective diagram of a device for nucleic acid amplification reaction when sample-dripping in an embodiment of the present invention; FIG. 2 is a perspective diagram of a measurement apparatus; FIG. 3 is a ground plan showing the principle of the measurement apparatus; and FIG. 4 is an exploded perspective view of the device for nucleic acid amplification reaction.

The device for nucleic acid amplification reaction 10 includes the following elements.

As shown in FIG. 1, the upper casing 100 includes an upper surface provided with the sample-dripping portion 101 receiving a liquid sample that may contain nucleic acid dripped from the nozzle 800.

An operator holds with his/her hand 802 the extraction container 801 storing the liquid sample containing the nucleic acid in a direction wherein the nozzle 800 faces downward, and drips a suitable amount of the liquid sample from the nozzle 800 onto the sample-dripping portion 101.

The discharge port 101a is opened at the lowest part of the sample-dripping portion 101, and the filter 301 is positioned right below the discharge port 101a.

The reaction tube 200 projects outwardly from a left end part of FIG. 1, possesses a storage space therein, and is formed capable of being installed within the measurement apparatus 700.

The filter 301 thereon carries the nucleic acid contained in the liquid sample.

The filter-supporting body 300 is stored inside of a casing including: the upper casing 100; and the lower casing 600, and supports the filter 301 in a manner such that the filter 301 is capable of taking:

a contacting position wherein the filter 301 contacts with the liquid sample right below the discharge port 101a of the sample-dripping portion 101; and a reaction position wherein the filter 301 is positioned within the storage space of the reaction tube 200.

The absorbing material 401 can take:

a press-attaching position wherein the absorbing material 401 is press-attached to the filter 301 in the contacting position so that the filter 301 absorbs the liquid sample contacting therewith; and a separating position wherein the absorbing material 401 is removed from the press-attaching position so that the filter 301 is allowed to freely move.

The cleaning liquid pot 120 carries cleaning liquid therein. The breaking projection 111 projects from the cover for cleaning liquid pot 110 to the cleaning liquid pot 120.

When the breaking projection 111 breaks through an aluminum seal of the cleaning liquid pot 120, the cleaning fluid within the cleaning liquid pot 120 can be discharged to the sample-dripping portion 101 via the chute 101b provided so as to face the sample-dripping portion 101.

Next referring to FIG. 2 and FIG. 3, the measurement apparatus 700 will now be explained.

As shown in FIG. 2, the measurement apparatus 700 in this embodiment is formed in a shape of a substantial trapezoid box including a front face inclined in a diagonally upper direction of about 30 degrees, and the monitor screen 702 and the door 705 are arranged on the front face of the box.

The monitor screen 702 shows the current operation situation for the review of the operator. Needless to say, a printer function may be added, if needed.

The door 705 is provided in order to protect the internal structure of the measurement apparatus 700 from the outside. In this embodiment, an upper edge frame of the door 705 is openably and closably mounted onto the top plate section of the measurement apparatus 700 with a hinge (not shown).

As shown in FIG. 2 when the door 705 is opened, a right part of the front surface of the measurement apparatus 700 is exposed to the outside.

The insertion port 701 into which the device 10 can be inserted is arranged at the right part.

After having dripped the liquid sample as shown in FIG. 1, the operator holds the device attaching part 102 of the device 10 in a direction that the reaction tube 200 faces forward so as to insert the device 10 through the insertion port 701.

As mentioned above, since the insertion port 701 is inclined in a diagonally upper direction of about 30 degrees, the device 10 is also set up being inclined similar thereto.

After that, it is sufficient for the operator to enter operation instructions to the measurement apparatus 700. Processes required for nuclear amplification reaction are automatically performed within the measurement apparatus 700.

The device 10 is set into the measurement apparatus at the angle of about 30 degrees, and the reaction tube is firmly settled in the temperature control block of the measurement apparatus.

The device 10 is obliquely at the angle inserted into the measurement apparatus 700. The reason why is as follows.

The dripped liquid sample does not spill out from the sample-dripping portion 101. And, in the inside of reaction tube 200, the reagent 201 required for nucleic acid amplification reaction remains at the temperature control block 703. The angle is introduced in order to maintain this situation.

When the angle is too large and almost perpendicular, the reagent 201 within the reaction tube 200 is stored at the bottom thereof and may easily touch temperature control block 703. Although the reaction may proceed correctly, there is a risk that the dripped liquid sample and/or the cleaning fluid flow/flows out of the device 10 in the middle of operation.

To the contrary, when the angle is too small and almost horizontal, the risk that the dripped sample spills out from the sample-dripping portion 101 is decreased.

There is, however, another risk that:

the sample 201 in the reaction tube 200 is not stored at the bottom well;

therefore temperature control by the temperature control block 703 is not effective; and the nucleic acid amplification reaction does not proceed well.

Upon having set the device 10 as mentioned above as shown in FIG. 3, a distal end of the reaction tube 200 is inserted into the temperature control block 703, and the device 10 keeps standing still within the measurement apparatus 700.

A Peltier element (not shown) is installed within the temperature control block 703, and the temperature of components containing nucleic acid in the reaction tube 200 is adjusted according to temperature conditions mentioned later.

The temperature control block 700 increases/decreases the temperature repeatedly by means of the Peltier element, and the temperature is transmitted to the reagent 201 within the reaction tube 200. Accordingly, it is preferable that the reaction tube 200 is composed of material that is as thin as possible and possesses high thermal diffusivity.

In order to be excellent in thermal responsiveness, it is preferable that the reaction tube 200 and the temperature control block 700 contact with each other as tightly as possible.

The fluorescence measurement unit 704 is stored in the measurement apparatus 700.

The unit 704 includes the following elements. The illuminator 704a emits fluorescence. The optical system 704c adjusts an optical path of the fluorescence to irradiate the fluorescence toward the components with in the reaction tube 200, and transmits reflected fluorescence. The light-receiving sensor 704b receives the transmitted fluorescence (fluorescence signals emitted by the reagent 201) to generate signals reflecting the same.

It is also possible to open a small window at a part of the temperature control block 703, and to measure the fluorescence signals emitted by the internal reagent 201 utilizing the fluorescence measurement unit 704.

Figure 6:
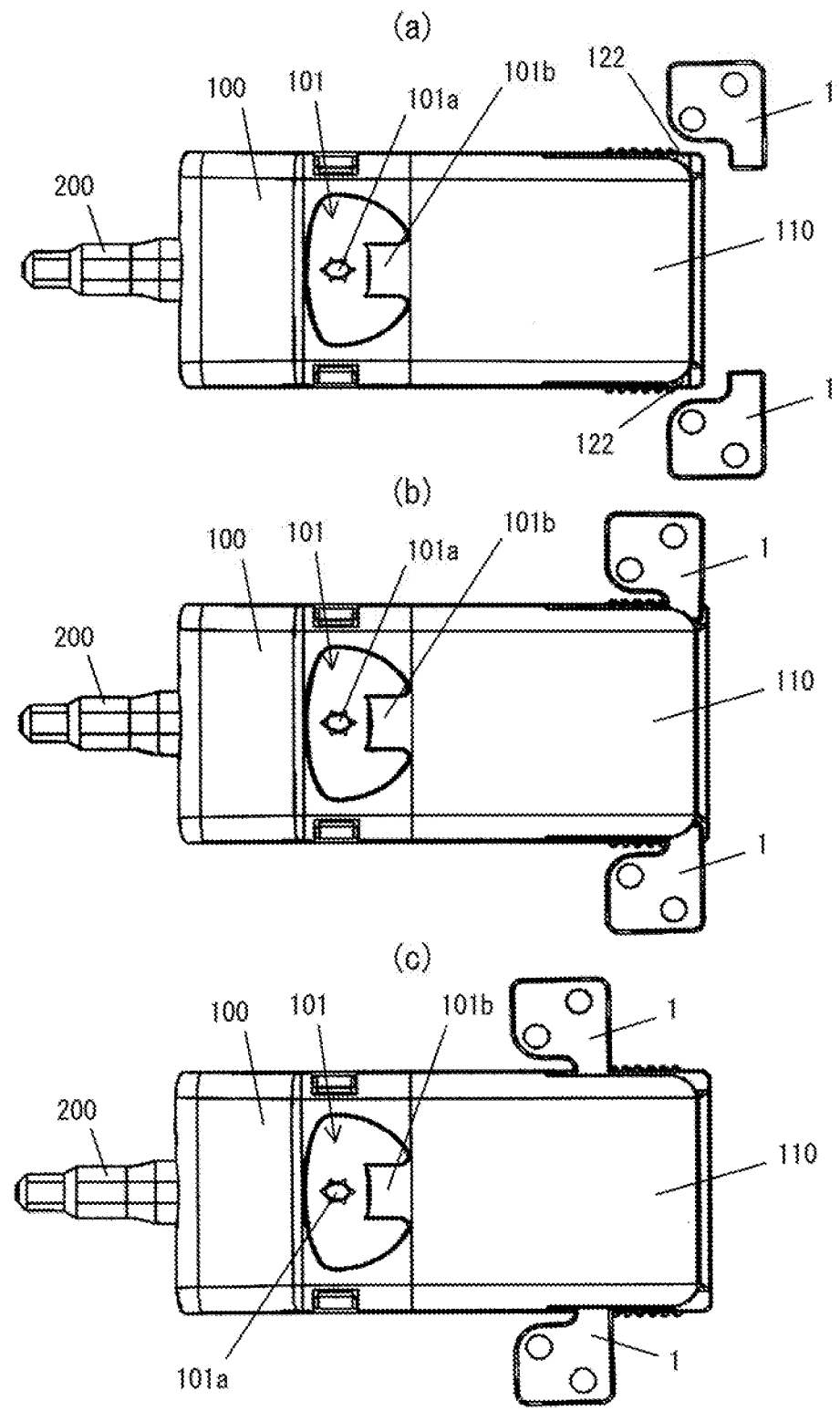

A linear drive system (not shown) driving the first pressing element 1, the second pressing element 2, and the third pressing element 3, respectively (See, FIG. 6, FIG. 10, and FIG. 11.) is provided within the measurement apparatus 700. The first pressing element 1, the second pressing element 2, and the third pressing element 3 respectively apply external force to the device 10 positioned within the measurement apparatus 700.

Figure 5:
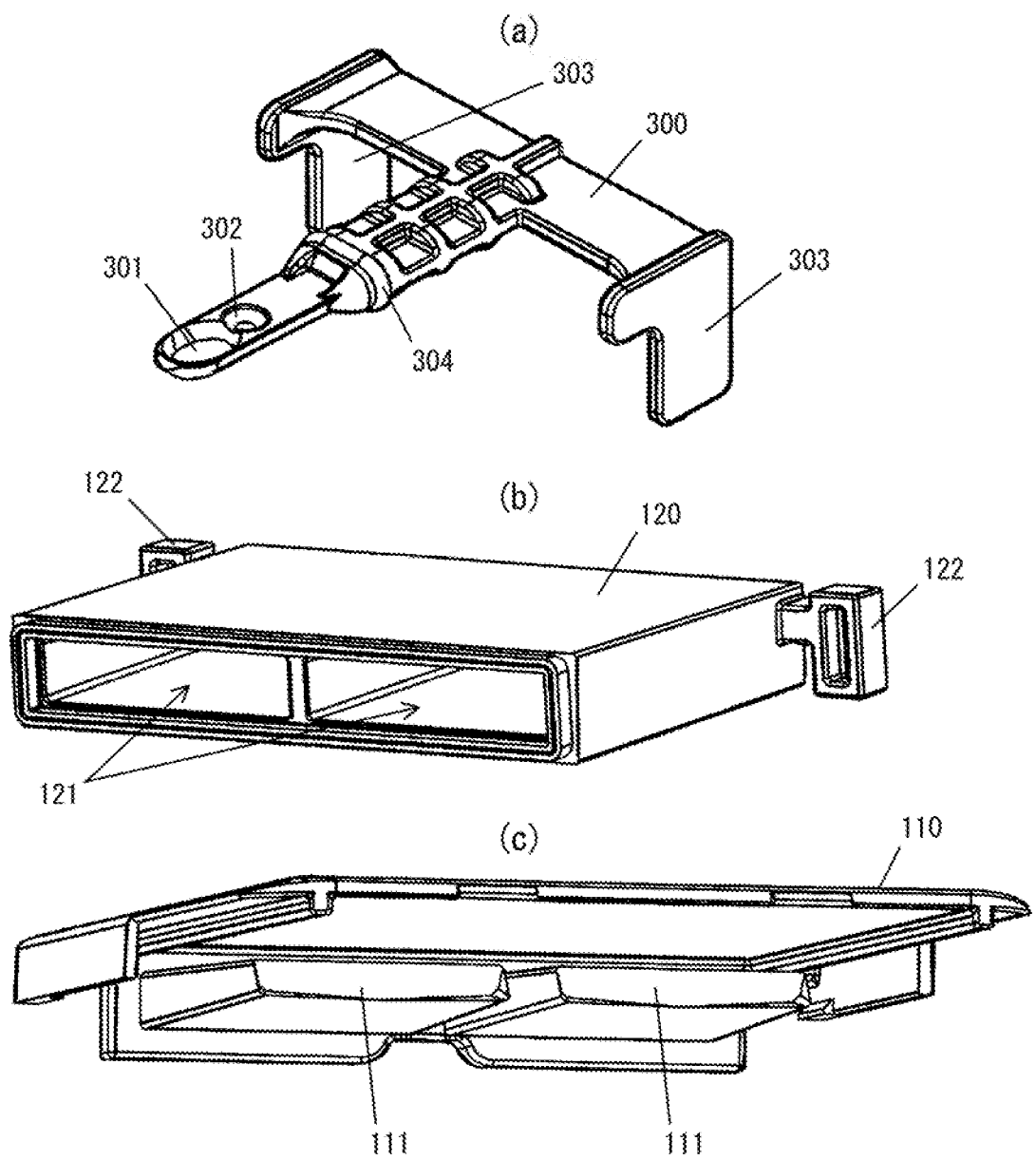

Next referring to FIG. 4, FIG. 5, and FIG. 8, details of the internal structure (especially a low portion) of the device 10 will now be explained.

In FIG. 4, relationship of members in a perpendicular vertical direction is shown in a manner that generally corresponds to after having assembled.

The lowest member is the lower casing 600, and the lower casing 600 supports members above the same.

As shown in FIG. 8(b), in order to enable to insert the second pressing element 2, the opening 602 is opened at the bottom portion of the opposite side of the reaction tube 200.

A pair of stoppers 601 and 601 are formed upward projectingly at the both sides of the opening 602.

The support plate 500 is placed right above the lower casing 600.

A pair of supports 501 and 501 are erected from the support plate 500 to support the lower surface on the placing part 402 of the absorbing material installation plate 400 above the support plate 500.

A pair of ribs are formed at the opposite side of the reaction tube 200 of the support plate 500 in a manner such that the opening 602 is not closed thereby.

The distal ends of the pair of ribs are formed to be the lock member 502 outwardly folded in the shape of a hook.

As shown in FIG. 8(b), the pressing part 503 is formed in the central part of the pair of ribs.

In a normal state as shown in FIG. 8(b), the lock member 502 and the stopper s 601 and 601 are engaged with each other, and the support plate 500 does not move in a longitudinal direction to the lower casing 600.

To the contrary, when the pressing element 2 is inserted within the opening 602 to apply external force (toward the reaction tube 200) onto the pressing part 503 in the longitudinal direction, the lock member 502 is elastically deformed inward to be released from the stoppers 601 and 601.

Thus, the support plate 500 becomes to be able to move relatively by a distance "d" at the maximum to the lower casing 600.

In an initial state, the absorbing material installation plates 400 belong to members in an intermediate stage.

The absorbing material installation plate 400 is a member supporting the absorbing material 401 (components thereof will be explained in full detail later.) absorbing liquid, and has the same width at the opposite side of the reaction tube 200 until the step part 403.

Ahead of there, the neck part 404 is formed to be narrower than the above, and again the placing part 402 is formed to have width wider than that of the neck part 404.

Figure 9:
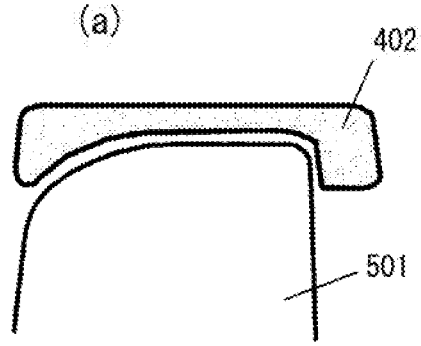
Figure 9:
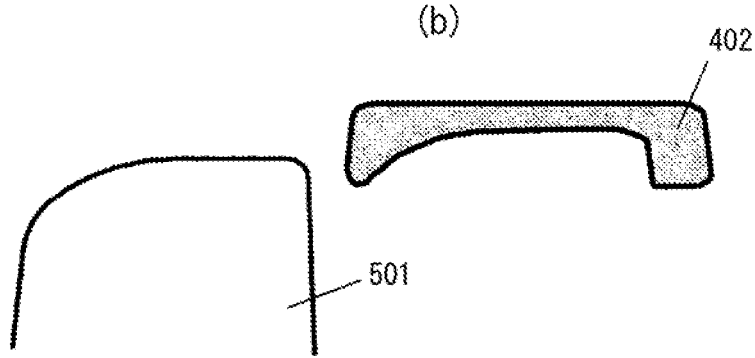

Herein, in a normal state as shown as enlargements in FIG. 9(a), the placing part 402 is placed on the top part of the support 501.

To the contrary, when the second pressing element 2 pushes the pressing part 503 to release the engagement as mentioned above, the support plate 500 moves by the distance "d" at the maximum in the longitudinal direction.

The absorption plate installation board 400 is, however, formed not able to move in the longitudinal direction. Accordingly as shown in FIG. 9(b), the support 501 and the placing part 402 are separated with each other, and the support 501 runs into the neck part 404.

As a result, the absorbing material installation plate 400 loses the support thereof, and naturally drops by its gravity (toward the lower stage) to overlap with the support plate 500.

As shown in FIG. 4, the reaction tube 200 of the device 10 inserted in the measurement apparatus 700 is firmly fixed to the internal temperature control block 703 in the measurement-apparatus 700.

The device 10 is assembled as shown in FIG. 4.

The device 10 includes: the upper casing 100 and the lower casing 600 being combined with each other to form the casing; and the reaction tube 200 projecting from the casing. The upper casing 100 is provided with: the sample-dripping portion 101 and; the device attaching part 102.

The cleaning liquid pot 120 and the cover for cleaning liquid pot 110 are attached with the upper casing 100 as a structure for flushing the cleaning fluid.

In the inside of the device 10, the filter-supporting body 300, the absorbing material installation plate 400, the support plate 500, and so on are installed. These members are for: catching and washing target genes from the sample dripped onto the sample-dripping portion 101; and further making the washed genes move toward the reaction tube 200.

Hereinafter, the further details will now be explained.

FIG. 5(a) is a perspective diagram of the filter-supporting body in the embodiment of the present invention, FIG. 5(b) is a perspective diagram of the cleaning liquid pot, and FIG. 5(c) is a perspective diagram of the cover for cleaning liquid pot.

As shown in FIG. 5(a), a hole is opened at a distal end of the filter-supporting body 300, and the filter 301 is stuck on this hole in a manner such that liquid can pass there-through.

It is preferable that silica particles are applied onto the filter 301 so that genes can be caught by the filter 301 with high efficiency.

It is also preferable that dried reagent components required for nucleic acid amplification reaction are applied and fixed onto the reagent application part 302 adjacent to the filter 301.

All of the reagent components may be stored within the tube 200. However, in order to improve stability more, it is preferable that all of the reagent components not stored therein but a part of the reagent components are separated therefrom to be set up. Accordingly, it is sufficient that at least the part of the reagent components are applied thereonto, if needed.

In order to prevent the liquid sample within the reaction tube 200 from evaporating during the amplification reaction, the "O" ring 304 is a seal member firmly sealing the filter-supporting body and the reaction tube so that the filter-supporting body and the reaction tube contact with each other tightly. Of course, a conventional seal member other than the "O" ring may be used instead thereof.

Next as shown in FIG. 5(b), cleaning fluid for washing the genes caught by the filter 301 is dispensed to the cleaning liquid pot 120, and the injecting port 121 thereof is closed with an aluminum seal.

A pair of protrusions 122 and 122 projecting outwardly are provided with side surfaces of the cleaning liquid pot 120, respectively. This arrangement is thus configured to make the liquid pot 120 move.

As shown in FIG. 6(a) through FIG. 6(c), when the first pressing element 1 pressing the projections 122 moves, the cleaning liquid pot 120 also moves within the device 10.

As a result of this movement (See, FIG. 5(c).), the breaking projection 111 provided from the cover for cleaning liquid pot 110 to the cleaning liquid pot 120 breaks through the aluminum seal closing the injecting port 121, and the cleaning fluid flows into the sample-dripping portion 101 via the chute 101b.

Herein, the breaking projection 111 has a size occupying almost all of the volume of the cleaning liquid pot 120. Accordingly, the cleaning fluid within the cleaning liquid pot 120 is pushed out by the breaking projection 111, and almost all of the cleaning fluid flows by compulsion into the sample-dripping portion 101.

Figure 7:
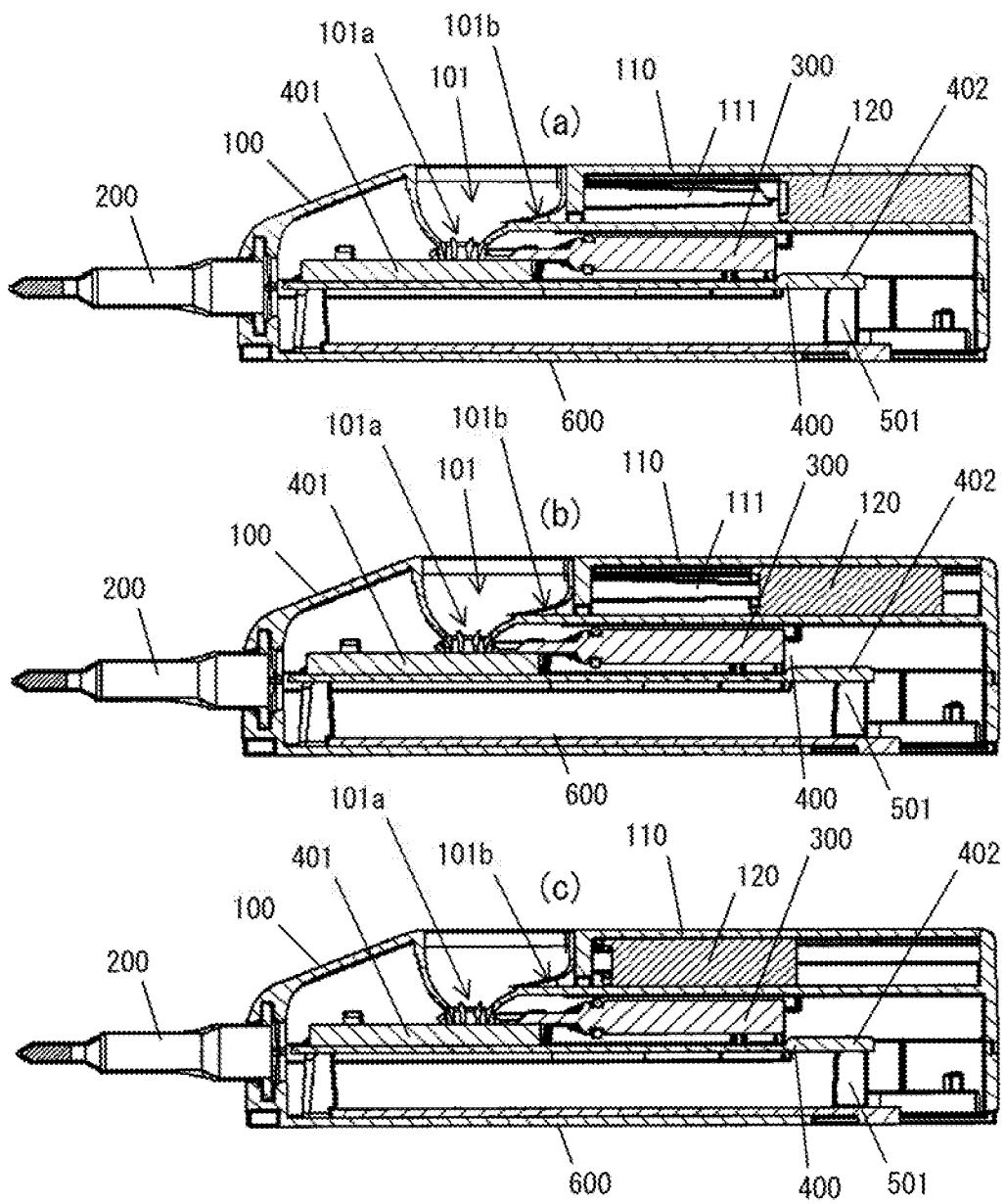

FIG. 7(a) through FIG. 7(c) are sectional views corresponding to FIG. 6(a) through FIG. 6(c), respectively.

In this embodiment, the breaking projection 111 is an integral molded item with the cover for cleaning liquid pot 110, is also installed within the cover for cleaning liquid pot 110, and breaks through the sealing member of the cleaning liquid pot 120.

The present invention is not limited to such a structure. In other words, it is enough that storage and supply of the cleaning fluid can be carried out by means of a conventional structure other than the above instead thereof.

As long as a similar function to the above can be achieved, both of the driving mechanism of the measurement apparatus 700, and the movement of the cleaning liquid pot 120 are not limited to this example.

Figure 8:
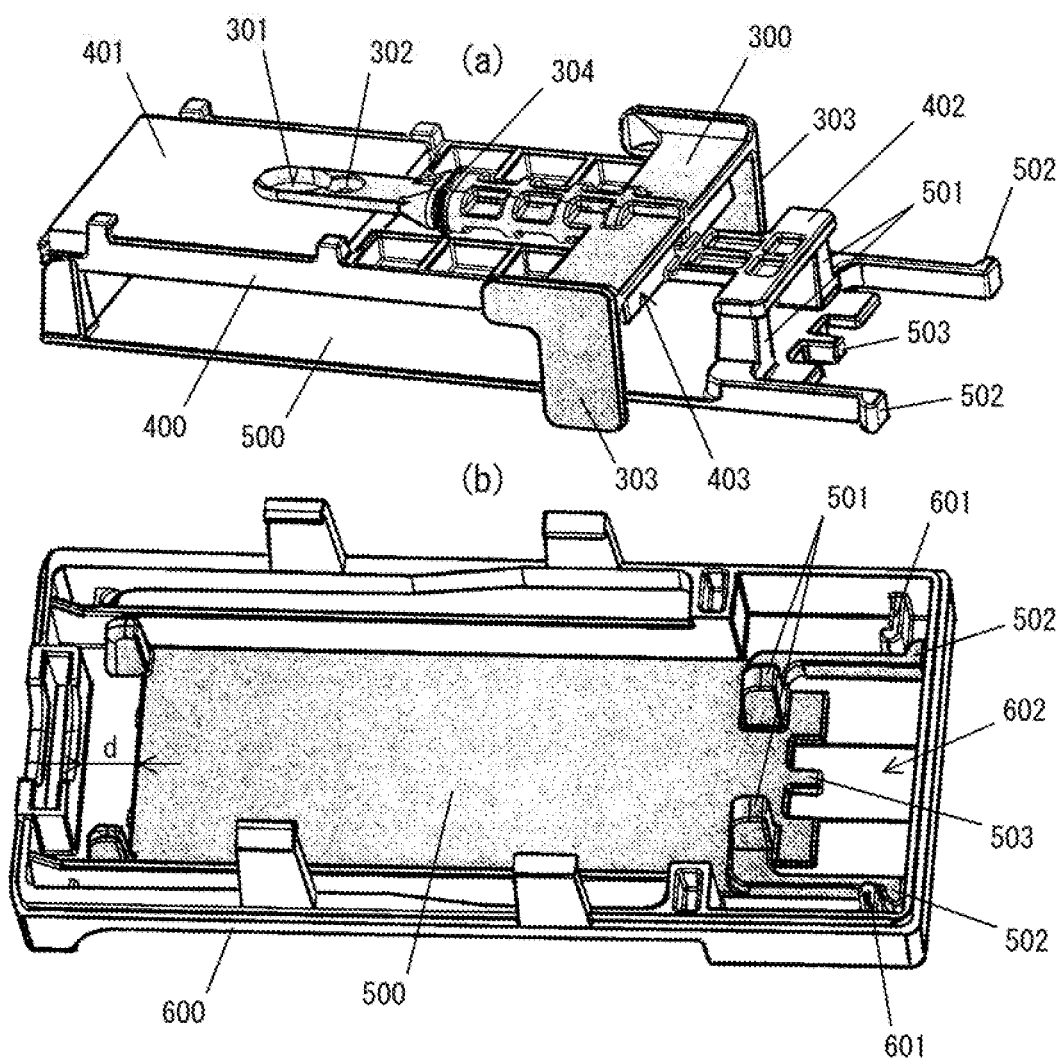

FIG. 8(*a*) shows positional relationship of the filter-supporting body 300, the absorbing material 401, and the support plate 500.

The absorbing material 401 is composed of comparatively soft material, such as filter paper, polymeric absorbing material, glass fiber filter paper, or the like, and absorbs the dripped liquid sample and the cleaning fluid flowing out thereafter through the filter 301.

The absorbing material installation plate 400 that the absorbing material 401 has been fixed thereon is supported by a pair of supports 501 and 501 of the support plate 500 to be held in a lifted state within the device 10. In this way, the absorbing material 401 is arranged within the device in a manner such that the absorbing material 401 is firmly press-attached to a lower surface of the filter 301.

Figure 10:
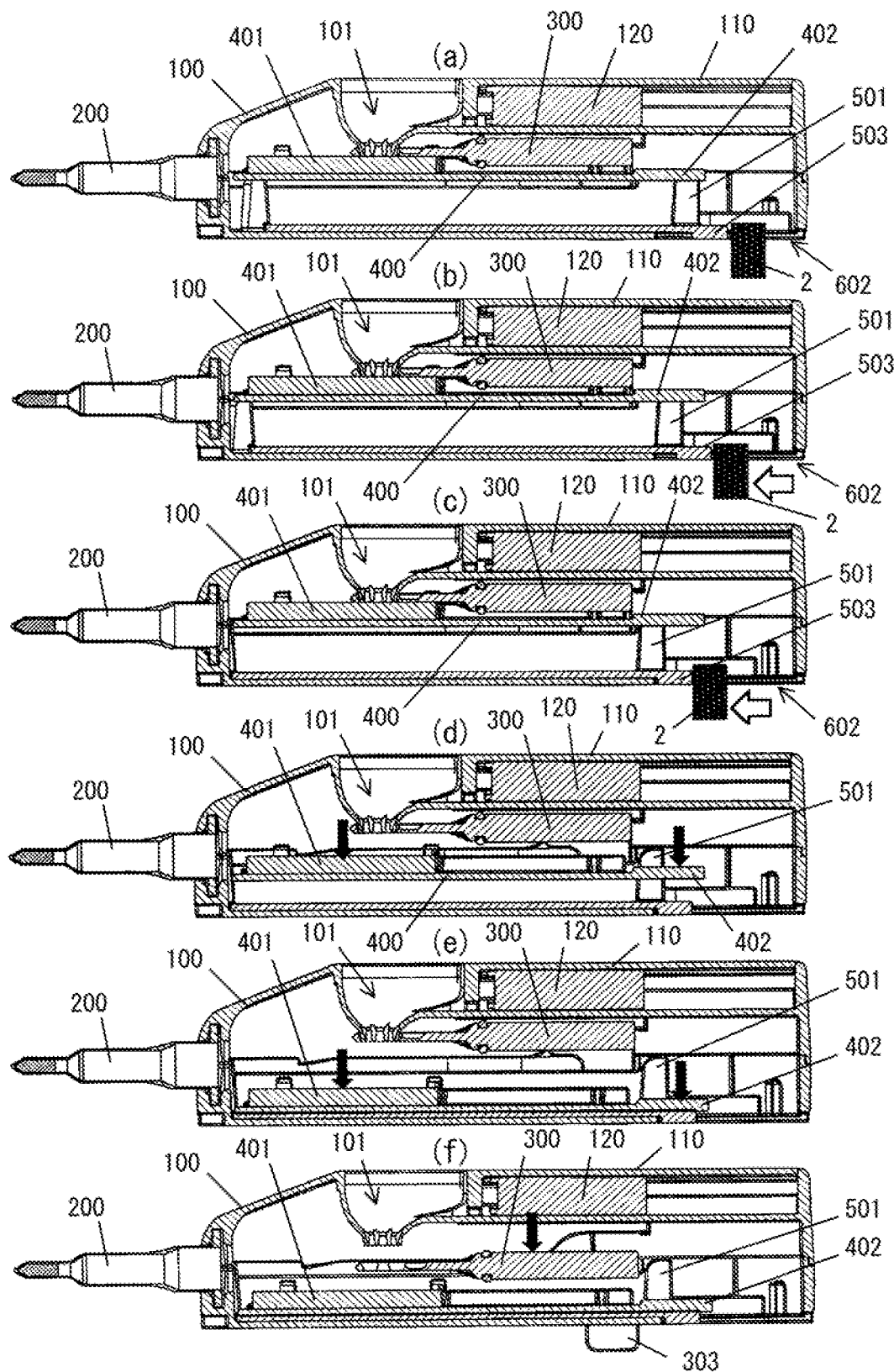

FIG. 10(*a*) through FIG. 10(*f*) are sectional views showing the internal states of the device 10 when the second pressing element 2 moves within the device 10.

When the pressing element 2 is inserted from the opening 602 of the lower casing 600 to apply force to the pressing part 503 of the support plate 500, the support plate 500 moves from a first position of FIG. 10(*a*) via a second position of FIG. 10(*b*) to a third position of FIG. 10(*b*).

When the support 501 is separated from the absorbing material installation plate 400, the absorbing material installation plate 400 loses the support thereof to fall toward the lowest stage (See, a position of FIG. 10(*e*).) via a position of FIG. 10(*d*).

At the same time, the filter-supporting body 300 also falls toward a position of FIG. 10(*f*) to overlap with the lower casing 600.

In this way, the filter-supporting body 300 becomes to be in a movable state from the press-attaching state, and a lower part of the driving rib 303 projects further downward from the lower casing 600 via a slit (not shown) of the lower casing 600.

Figure 11:
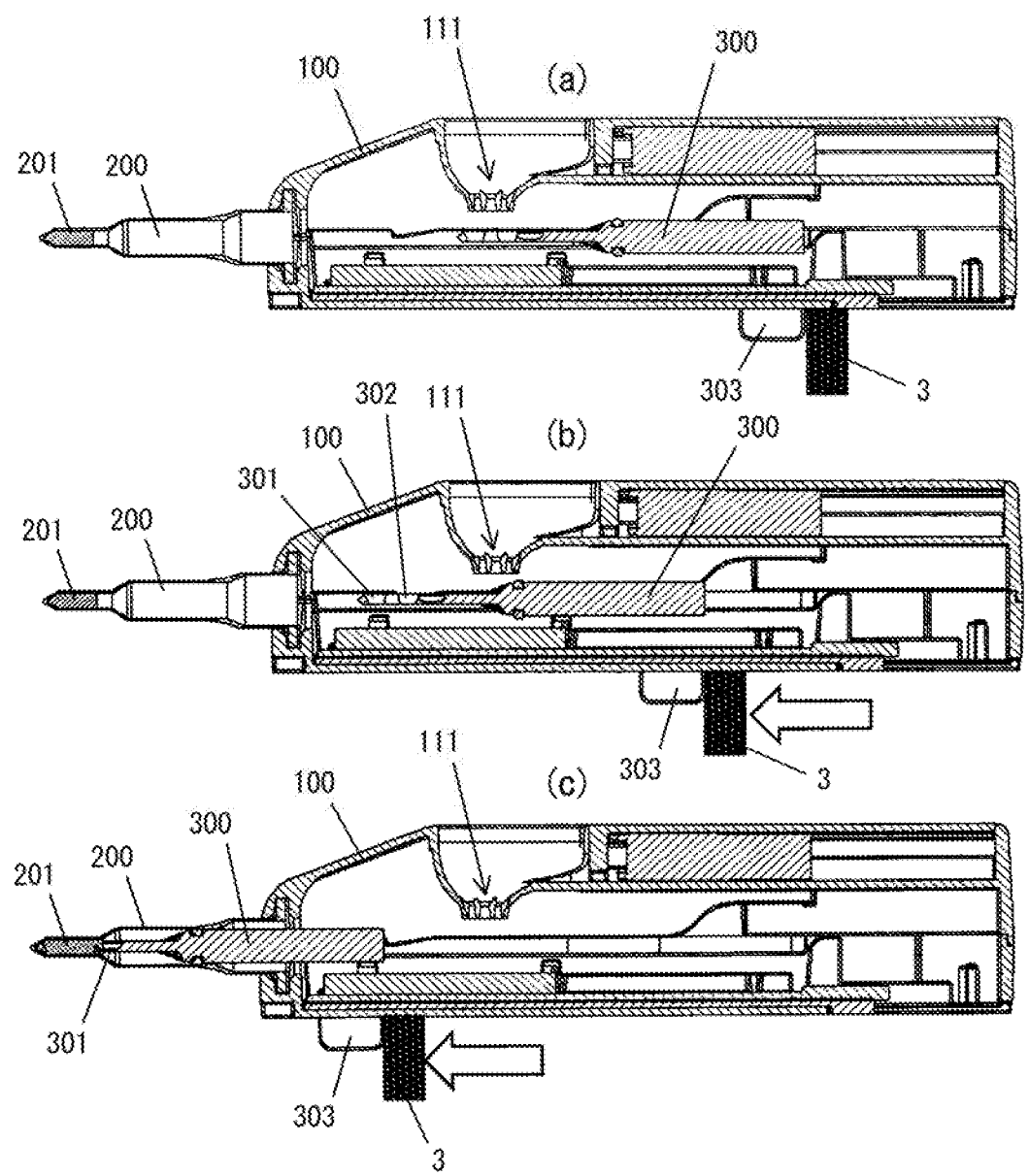
Figure 12:
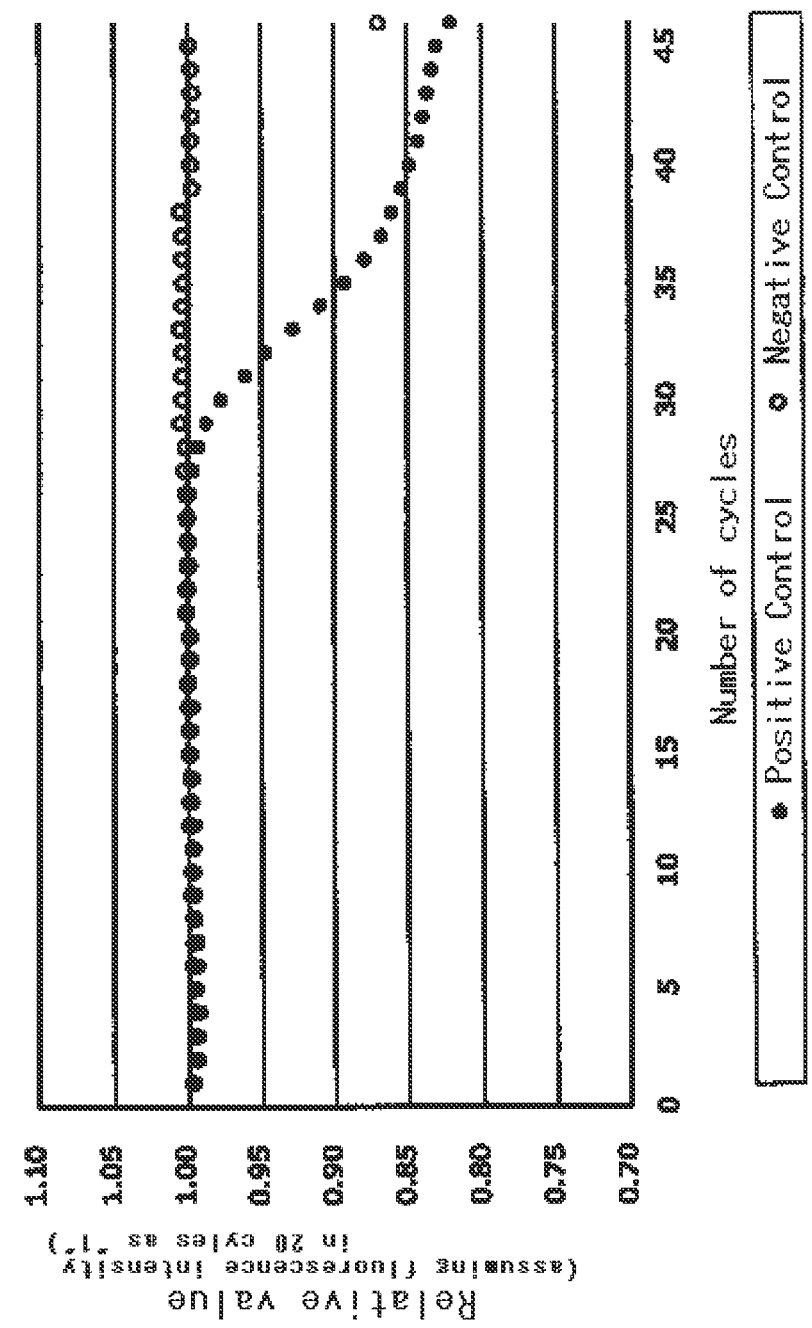

After that as shown in FIG. 11(*a*), when the third pressing element 3 pushes the lower part of the driving ribs 303 and 303 projecting downward form the lower casing 600, the filter-supporting body 300 moves from a position of FIG. 11(*a*) via a state of FIG. 11(*b*). And, the filter 301 at the distal end and the reagent application part 302 move to the end (See, a position of FIG. 11(*c*).) of movement.

As a result as shown in FIG. 11(*c*), the filter 301 and the nucleic acid carried by the same are completely pushed into the reagent 201 of the reaction tube 200.

The reagent 201 required for nucleic acid amplification reaction is stored within the reaction tube 200. Accordingly, in order to prevent the reagent within the reaction tube 200 from evaporating during the amplification reaction, it is preferable that an inlet toward the reagent 201 is closed with an aluminum seal.

In this case, a distal end of the filter-supporting body 300 may be formed in a sharp shape operable to break through the aluminum seal.

The components of the reagent 201 may contain: enzyme for amplification reaction; substrate; buffer components; specific primer sets; and fluorescent-labeling probes or the like at a detection region. In order to improve stability in preservation, a part of these components of the reagent 201 may be installed within the reaction tube 200, and the remainder of these components may be installed within the reagent application part 302 of the filter-supporting body 300 to be separated therewith.

In a liquid state, the reagent 201 within the reaction tube 200 may not stand still at the bottom portion suitable for the reaction caused by vibration or the like during transport and/or process with respect to the device 10. Accordingly, it is preferable that the reagent 201 is fixed in a solid state and/or a gelled state so that the reagent 201 cannot easily move until the beginning of the reaction.

It is preferable that, upon manufacturing the reagent, hot-melt polymeric compound (such as agarose or the like) is heated and dispensed into the tube 200 with the components of the reagent 201 to be fixed and/or gelled by cooling the same after that.

In this way, even if vibration, rotation, and so on upon transport the device 10 try to make the device 10 to move, the reagent 201 cannot move to be surely held at the bottom portion of the reaction tube 200.

To the contrary, immediately before nucleic acid amplification reaction, by increasing the temperature to be 95 degrees Centigrade or the like, the gelled reagent 201 within the reaction tube 200 is dissolved to be in a liquid state, and the nucleic acid amplification reaction can be started at ease without any problems.

Thus, the device in this embodiment can be completed by arranging and assembling the members prepared as mentioned above as shown in FIG. 4.

(Measurement)

When the operator performs measurement actually, a liquid sample is collected with the extraction container 801, genes therein are extracted, and a necessary amount of the liquid sample is dripped onto the sample-dripping portion 101 of the upper casing 100 to be set to the dedicated measurement apparatus 700. This operation is very easy.

In order to store the solution of the sample-dripping portion 101 and to ensure the amount of liquid upon the reaction, it is preferable that the device 10 is inserted into the measurement apparatus 700 inclined at the angle of 30 degrees to a horizontal direction.

After that, it is unnecessary for the operator to perform troublesome operation. On the contrary, all of necessary steps are automatically carried out by the dedicated measurement apparatus itself 700.

The genes within the dripped extraction liquid are caught by the silica particles on the filter 301 carried on the filter-supporting body 300.

The dripped liquid passes through the filter 301, and is absorbed and removed by the absorbing material 401 contacting with the lower surface and being installed on the filter 301.

After that, the first pressing element 1 of the measurement apparatus 700 pushes the cleaning liquid pot 120 within the device 10 to break through the aluminum seal. And, the cleaning fluid is discharged onto the sample-dripping portion 101 to wash the genes caught by the silica particles on the filter 301.

The cleaning fluid also passes through the filter 301 to be absorbed and removed by the absorbing material 401.

After that, the second pressing element 2 of the measurement apparatus 700 is driven to make the support plate 500 including the support 501 move.

Common movement of the support 501 and the support plate 500 causes to release the engagement between the support 501 and the placing part 402, thereby the absorbing material installation plate 400 falls toward the lowest stage.

At the same time, the filter-supporting body 300 also falls from the intermediate stage toward the lowest stage. As a result, the filter-supporting body 300 becomes in a movable state from the press-attaching state wherein the filter 301 is press-attached between the sample-dripping portion 101 of the upper casing 100 and the absorbing material 401.

After the filter-supporting body 300 has been allowed to move, movement of the third pressing element 3 of the measurement apparatus 700 causes the filter 301 to be pushed into the reagent 201 within the reaction tube 200.

In this way, the genes caught by the filter 301 are transported to the inside of the reaction tube 200. And then, by means of the reagent 201 within the reaction tube 200, the amplification reaction is started in the temperature control block 703 of the measurement apparatus 700.

Temperature conditions for gene amplification may be different according to measurement items. For example, first temperature of 95 degrees Centigrade and second temperature of 65 degrees Centigrade are repeated to occur annealing with the primers and reproduction reaction, thereby proceeding the nucleic acid amplification reaction.

In order to detect the nucleic acid amplification reaction, it is preferable that labeled probes or the like outputting signals upon specifically conjugating with amplified product are used.

Measurement of the signals may be easily made by means of the light-receiving sensor 704b of the measurement apparatus 700, the light-receiving sensor 704b being installed on a side surface of the reaction tube.

That is, the illuminator 704a of the fluorescence measurement unit 704 irradiates excited light from the side surface of the transparent reaction tube 200, and the light-receiving sensor 704b detects and measures a generated fluorescence amount.

It is preferable that the measurement apparatus 700 shows a measurement result on the monitoring screen 702, and/or further prints out a detection result.

EXAMPLES (Detection of P1 Genes Upon Diagnosis of *Mycoplasma pneumonia*)

How to detect P1 genes of *Mycoplasma pneumoniae* (pathogen of *Mycoplasma pneumonia*) by means of the device 10 according to the present invention will now be shown below.

(Manufacture of Device 10 for *Mycoplasma* Detection)

At a distal end of the filter-supporting body 300, a hole is opened and the filter 301 is carried thereby. In order to catch genes, the hole carries thereon the filter 301 composed of hydrophilic PTFE membrane cut into a shape of a band with size of 5×8 [mm].

40 [μg] of silica particles possessing 1 [μm] of an average particle diameter have been applied onto the membrane to be dried so that the genes can be caught with high efficiency.

8 [μL] of the reaction reagent 1 containing DNA polymerase has been applied to be dried onto the reagent application part 302 of the filter-supporting body 300.

1.2 [mL] of purified water as the cleaning fluid has been dispensed into the cleaning liquid pot 120, and the aluminum seal has been stuck onto the injecting port 121 to form a sealed body.

Polymeric absorbing material and glass fiber filter paper have been overlapped with each other as the absorbing material 401 to be cut into a size of 25 [mm]×25 [mm] and width of 2.5 [mm] to form the absorbing material. The absorbing material has been installed to complete the absorbing material installation plate 400.

Within the reaction tube 200, 50 [μL] of the reaction reagent 2 containing: agarose: primer sets for detecting *Mycoplasma*; and "Q" probes have been dispensed to be gelled. A mouth of the reaction tube 200 has been sealed with an aluminum seal to form a sealed body.

The filter-supporting body 300, the cleaning liquid pot 120, the absorbing material installation plate 400, and the reaction tube 200 have been thus prepared and have been combined with: the upper casing 100; the cover for cleaning liquid pot 120; the support plate 500; and the lower casing 600.

As shown in FIG. 4, the arrangement of the above has been made, and the device 10 for *Mycoplasma* measurement has been assembled.

(Measurement of *Mycoplasma*)

As a positive control, mixture has been used. After gene fragments coding P1 protein (membrane protein) derived from *Mycoplasma pneumoniae* (pathogen of *Mycoplasma pneumonia*) had been artificially composed, and plasmid DNA embedded into pMD20T vector has been added to physiological saline to produce the mixture. As a negative control, physiological saline itself has been used.

150 [μL] of the respective sample has been isolated to be added to 550 [μL] of extraction liquid containing chaotropic salt.

110 [μL] of the respective extracted liquid has been dripped onto the sample-dripping portion 101 of the upper casing 100 of the assembled device 10 for *mycoplasma* measurement. After hading confirmed that the dripped liquid had passed through and had been absorbed by the filter 301 completely, the filter has been inserted into the dedicated measurement apparatus 700.

The device 10 is inserted being inclined at the angle of about 30 degrees to a horizontal direction by a guide of the measurement apparatus 700. Within the measurement apparatus 700, the reaction tube 200 is positioned to the temperature control block 703 and the fluorescence measurement unit 704.

After that, the first pressing element 1 of the measurement apparatus 700 is moved to slide the cleaning liquid pot 120. Thereby, the aluminum seal of the cleaning liquid pot 120 is broken through to discharge the cleaning fluid to the sample-dripping portion 101.

The cleaning fluid washes the genes caught by the silica particles on the filter 301 to be absorbed by the absorbing material 401 below the filter 301.

After a liquid level sensor (not shown) of the measurement apparatus 700 has confirmed that the cleaning fluid have been filtered, the second pressing element 2 projecting inwardly from the opening 602 of the lower casing 600 moves to apply force to the pressing part 503.

Then, the engagement between the lock member 502 of the support plate 500 and the stoppers 601 and 601 are released, and the support plate 500 moves. In this way, the absorbing material installation plate 400 and the filter-supporting body 300 are changed from the press-attached fixed state to a movable removed state.

After that, the third pressing element 3 pushes the driving ribs 303 and 303 to make the filter-supporting body 300 move toward the end wherein the filter 301 and the reagent application part 302 are press-inserted into the reagent 201 within the reaction tube 200.

According to a series of operation mentioned above, the pre-dispensed reaction reagent 2, the reaction reagent 1 applied onto the reagent application part 302 of the filter-supporting body, and DNA of *Mycoplasma pneumoniae* conjugated with the silica articles on the filter 301 are mixed all together.

TABLE 1

| Conditions regarding PCR method | | |
|---|---|---|
| Reaction condition | Temperature(° C.) | Time (sec) |
| Initial denaturalization | 95 | 120 |
| Amplification reaction | 95 | 5 |
| (1-45 cycles) | 70 | 15 |
| 2nd target-detecting step | 95 | 10 |
| | 42.5 | 20 |

After the third pressing element 3 have moved, the measurement apparatus 700 repeatedly increases/decreases temperature of the temperature control block 703 in accordance with the temperature profile shown in (Table 1) to begin PCR within the reaction tube 200 immediately.

FIG. 12 shows a graph showing measurement results of the positive control and the negative control in the embodiment according to the present invention.

When a "Q" probe is conjugated with a target gene, it quenches light. Accordingly, it is assumed that fluorescence intensity becomes smaller as cycles with respect to the positive control progress.

With respect to the positive control of FIG. 12, quenching caused by amplification of the target gene is observed from the neighborhood 28 cycles. To the contrary, with respect to the negative control, quenching is not observed until 45 cycles.

As discussed in detail above, the present invention relates to the device for the nucleic-acid amplifying method available to transform product of the genetic screening regarding in vitro diagnostic into the POCT mode.

The general genetic screening is an examination method excellent in both of sensibility and specificity. However, the general genetic screening requires expensive measurement apparatuses and the skilled art, and is in a state that cannot be at ease developed to small-scaled hospitals and/or medical practitioners.

To the contrary, upon using the device 10 according to the present invention, it is sufficient to drip a liquid sample after extraction and to set the device to the dedicated measurement apparatus 700 only.

Within the device 10, it is possible to perform the steps of: catching genes; washing the same; amplification reaction regarding the same; and detection of the same. The problem of contamination can be also solved. Very simple, and a short-time inspection are attained. Due to the low cost thereof, the device is thus likely to develop widely in many medical scenes.

BRIEF DESCRIPTION OF THE DRAWINGS

FIG. 1 is a perspective diagram of a device for nucleic acid amplification reaction when dripping a sample in an embodiment of the present invention;

FIG. 2 is a perspective diagram of the measurement apparatus in the embodiment of the present invention;

FIG. 3 is a ground plan showing the principle of a measurement apparatus in the embodiment of the present invention;

FIG. 4 is an exploded perspective view of the device for nucleic acid amplification reaction in the embodiment of the present invention;

FIG. 5(*a*) is a perspective diagram of a filter-supporting body in the embodiment of the present invention;

FIG. 5(*b*) is a perspective diagram of a cleaning liquid pot in the embodiment of the present invention;

FIG. 5(*c*) is a perspective diagram of a cover for cleaning liquid pot in the embodiment of the present invention;

FIG. 6(*a*) is a first explanatory diagram of a first pressing element in the embodiment of the present invention;

FIG. 6(*b*) is a second explanatory diagram of the first pressing element in the embodiment of the present invention;

FIG. 6(*c*) is a third explanatory diagram of the first pressing element in the embodiment of the present invention;

FIG. 7(*a*) is a first explanatory diagram of the cleaning liquid pot in the embodiment of the present invention of operation;

FIG. 7(*b*) is a second explanatory diagram of the cleaning liquid pot in the embodiment of the present invention of operation;

FIG. 7(*c*) is a third explanatory diagram of the cleaning liquid pot in the embodiment of the present invention of operation;

FIG. 8(*a*) is a perspective diagram of the filter-supporting body and absorbing material in the embodiment of the present invention;

FIG. 8(*b*) is a perspective diagram of a lower casing and a support plate in the embodiment of the present invention;

FIG. 9(*a*) is a first explanatory diagram of a support in the embodiment of the present invention;

FIG. 9(*b*) is a second explanatory diagram of the support in the embodiment of the present invention;

FIG. 10(*a*) is a first explanatory diagram of the absorbing material in the embodiment of the present invention;

FIG. 10(*b*) is a second explanatory diagram of the absorbing material in the embodiment of the present invention;

FIG. 10(*c*) is a third explanatory diagram of the absorbing material in the embodiment of the present invention;

FIG. 10(*d*) is a fourth explanatory diagram of the absorbing material in the embodiment of the present invention;

FIG. 10(*e*) is a fifth explanatory diagram of the absorbing material in the embodiment of the present invention;

FIG. 10(*f*) is a sixth explanatory diagram of the absorbing material in the embodiment of the present invention;

FIG. 11(*a*) is a first operation explanatory diagram of the filter-supporting body in the embodiment of the present invention;

FIG. 11(*b*) is a second operation explanatory diagram of the filter-supporting body in the embodiment of the present invention;

FIG. 11(*c*) is a first operation explanatory diagram of the filter-supporting body in the embodiment of the present invention; and FIG. 12 is a graph showing a measurement result with respect to a positive control and a negative control in the embodiment of the present invention.

BRIEF DESCRIPTION OF SYMBOLS

1: First Pressing Element
2: Second Pressing Element
3: Third Pressing Element
10: Device for Nucleic Acid Amplification Reaction
100: Upper Casing
101: Sample-dripping Portion
101*a:* Discharge port
101*b:* Chute 102: Reaction Device-holding Portion
103: Stopper
110: Cover for Cleaning Liquid Pot
111: Breaking Projection
120: Cleaning Liquid Pot
121: Injecting Port
122: Projection
200: Reaction Tube
201: Reagent
300: Filter-supporting Body
301: Filter
302: Reagent Application Part
303: Driving Rib
304: "O" Ring
400: Absorbing Material Installation Plate
401: Absorbing Material
500: Support Plate
501: Support
502: Lock Member
503: Pressing Part
600: Lower Casing
601: Stopper
602: Opening
700: Measurement Apparatus
701: Insertion Port
702: Monitor Screen
703: Temperature Control Block
704: Fluorescence Measurement Unit
704a: Illuminator
704b: Light-Receiving Sensor
705: Door
800: Dripping Nozzle
801: Extraction Container
802: Hand

What is claimed is:

1. A device for nucleic acid amplification reaction, comprising:
    a casing with an upper surface including a sample-dripping portion capable of receiving a liquid sample dripped from a nozzle and containing nucleic acid;
    a reaction tube: outwardly projecting from an end of the casing; including a storage space therein; and being formed so as to be installed within a measurement apparatus;
    a filter carrying thereon the nucleic acid contained in the liquid sample;
    a filter-supporting body stored within the casing to support the filter in a manner such that the filter is capable of taking:
        a contacting position wherein the filter contacts with the liquid sample right below the sample-dripping portion; and
        a reaction position wherein the filter is positioned within the storage space of the reaction tube; and
    an absorbing material capable of taking:
        a press-attaching position wherein the absorbing material is press-attached to the filter in the contacting position so that the filter absorbs the liquid sample contacting therewith; and
        a separating position wherein the absorbing material is removed from the press-attaching position so that the filter is allowed to freely move,
        wherein the filter-supporting body falls downward within the casing, thereby the absorbing material moves from the press-attaching position to the separating position.

2. The device for nucleic acid amplification reaction as defined in claim 1, further comprising:
    a cleaning liquid pot carrying cleaning fluid therein; and
    a breaking projection allowing the cleaning fluid within the cleaning liquid pot to flow toward the sample-dripping portion.

3. The device for nucleic acid amplification reaction as defined in claim 1, wherein a pressing part drives the filter-supporting body to be supported so that the filter-supporting body is allowed to move from the contacting position to the reaction position.

4. The device for nucleic acid amplification reaction as defined in claim 1, wherein the reaction tube is composed of a transparent material.

5. The device for nucleic acid amplification reaction as defined in claim 1, wherein the reaction tube holds at least a part of reagent required for the nucleic acid amplification reaction.

6. The device for nucleic acid amplification reaction as defined in claim 5, wherein the reagent required for the nucleic acid amplification reaction contains hot-melt polymeric compound that is solidified and/or gelled before the nucleic acid amplification reaction, and that is heated to become liquid in the nucleic acid amplification reaction, the reagent being held within the reaction tube.

7. The device for nucleic acid amplification reaction as defined in claim 1, wherein the absorbing material is composed of a water absorptive soft material selecting from the group consisting of filter paper; a polymeric absorbing material; and
    glass fiber filter paper.

8. The device for nucleic acid amplification reaction as defined in claim 1, wherein a silica particle is fixed to the filter.

9. The device for nucleic acid amplification reaction as defined in claim 1, wherein the filter is composed of polymeric membrane.

10. The device for nucleic acid amplification reaction as defined in claim 9, wherein the filter is composed of hydrophilic PTFE (polytetrafluoroethylene).

11. The device for nucleic acid amplification reaction as defined in claim 1, wherein the filter-supporting body holds reagent required for the nucleic acid amplification reaction.

* * * * *

UNITED STATES PATENT AND TRADEMARK OFFICE
CERTIFICATE OF CORRECTION

PATENT NO. : 11,618,028 B2
APPLICATION NO. : 16/463517
DATED : April 4, 2023
INVENTOR(S) : Kenji Narahara et al.

It is certified that error appears in the above-identified patent and that said Letters Patent is hereby corrected as shown below:

In the Specification

In Column 3, Line 32, after "thereof", insert --.--

In Column 10, Line 25, delete "700" and insert --703--

In Column 10, Line 33, delete "700" and insert --703--

In Column 11, Line 17, delete "stopper s" and insert --stoppers--

In the Claims

In Column 20, Claim 7, Line 41, after "and", delete "¶"

Signed and Sealed this
Twenty-seventh Day of June, 2023

Katherine Kelly Vidal
*Director of the United States Patent and Trademark Office*